(12) United States Patent
Gladwell et al.

(10) Patent No.: US 7,018,818 B2
(45) Date of Patent: Mar. 28, 2006

(54) INTERMEDIATES IN THE PREPARATION OF THERAPEUTIC FUSED BICYCLIC AMINO ACIDS

(75) Inventors: Iain Robert Gladwell, Gravesend (GB); Alan John Pettman, Dover (GB)

(73) Assignee: Pfizer Inc., New York, NY (US)

( * ) Notice: Subject to any disclaimer, the term of this patent is extended or adjusted under 35 U.S.C. 154(b) by 25 days.

(21) Appl. No.: 10/677,836

(22) Filed: Oct. 2, 2003

(65) Prior Publication Data

US 2004/0138498 A1 Jul. 15, 2004

Related U.S. Application Data

(60) Provisional application No. 60/421,868, filed on Oct. 28, 2002.

(30) Foreign Application Priority Data

Oct. 4, 2002 (GB) .................................... 0223070

(51) Int. Cl.
*C12P 7/44* (2006.01)
*C12P 7/62* (2006.01)
*C07C 57/26* (2006.01)

(52) U.S. Cl. ...................... 435/136; 435/135; 435/128; 560/119; 562/501

(58) Field of Classification Search ................ 562/501; 560/119; 435/135, 136, 128
See application file for complete search history.

(56) References Cited

FOREIGN PATENT DOCUMENTS

| EP | 1226820 A1 | 7/2002 |
|---|---|---|
| WO | WO 99/21824 | 5/1999 |
| WO | WO 01/28978 A1 | 4/2001 |
| WO | WO 02/085839 A1 | 10/2002 |

OTHER PUBLICATIONS

Wallquist et al, Helvetica Chimica Acta, 1983, 66(6) 1876-90.*
Snider et al, J. Org. Chem. 1986, 51, pp3643-3652.*
Lortie, Biotechnology Advances, vol. 15(1), p. 1-15 (1997).*
Chen, L. Y., et al. "Study of Chiral Zuxiliaries for the Intramolecular [2+2] Cycloaddition of a Keteniminum Salt to an Olefinic Double Bond. A New Asymmetric Synthesis of Cyclobutanones." Tetrahedron Letters vol. 32. pp. 4467-4470, 1990.
Hoffman., H.M.R., et al. "Synthesis of Cyclobutylideneaccetic Esters Via Aluminum Chloride Promoted [2+2] Cycloadditions of Ethyl 2,3-Butadienoate to Olefin+" Tetrahedron Letters, vol. 22, No. 21, pp 1953-1956, 19881.
B. B. Snider, et al., "Lewis Acid Catalyzed Inter- and Intramolecular [2+2 Cycloadditions of Conjugated Allenic Esters", Journal of Organic Chemistry, 1986, pp 3643-3652, vol. 51, No. 19.
O. Wallquist, et al. "Conversion of Bicyclo [3.2.0]hept-2-en-6-on in Cyclopentadienylacetic Acid Derivatives", 1983, pp 1876-1889, vol. 66, No. 6.

* cited by examiner

*Primary Examiner*—Bernard Dentz
(74) *Attorney, Agent, or Firm*—Suzanne M. Harvey; David R. Kurlandsky; Charles W. Ashbrook

(57) ABSTRACT

The invention presents compounds of formula (I),

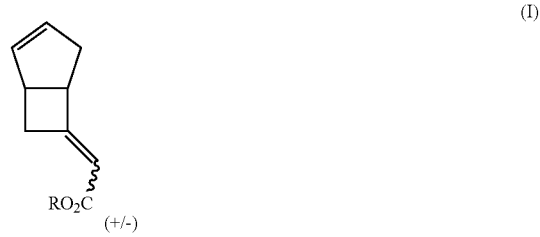

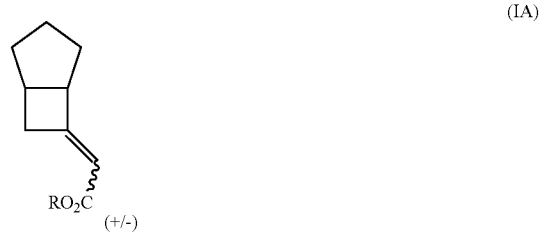

where R represents H or a suitable carboxylic acid protecting group, which are intermediates in the preparation of therapeutic fused bicyclic amino acids.

4 Claims, No Drawings

INTERMEDIATES IN THE PREPARATION OF THERAPEUTIC FUSED BICYCLIC AMINO ACIDS

This United States Utility Application claims the benefit of United Kingdom Application Number 0223070.4 filed Oct. 4, 2002 and U.S. Provisional Application No. 60/421,868 filed Oct. 28, 2002.

FIELD OF THE INVENTION

This invention relates to intermediates of novel cyclic amino derivatives useful as pharmaceutical agents and to processes for their production.

BACKGROUND TO THE INVENTION

International Patent Application Publication No. WO 99/21824 discloses cyclic amino acids that are useful in the treatment of epilepsy, faintness attacks, neurodegenerative disorders, depression, anxiety, panic, pain, neuropathological disorders, gastrointestinal disorders such as irritable bowel syndrome (IBS) and inflammation, especially arthritis. The compounds disclosed include those of the formula:

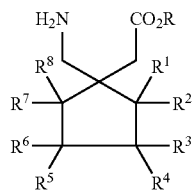

and salts thereof, in which: R is hydrogen or a lower alkyl; and $R^1$ to $R^8$ are each independently selected from hydrogen, straight or branched alkyl of from 1 to 6 carbons, phenyl, benzyl, fluorine, chlorine, bromine, hydroxy, hydroxymethyl, amino, aminomethyl, trifluoromethyl, —$CO_2H$, —$CO_2R^{15}$, —$CH_2CO_2H$, —$CH_2CO_2R^{15}$, —$OR^{15}$ wherein $R^{15}$ is a straight or branched alkyl of from 1 to 6 carbons, phenyl, or benzyl, $R^1$ to $R^8$ not being simultaneously hydrogen.

International Patent Application Publication No. WO0128978 describes a series of novel bicyclic amino acids, their pharmaceutically acceptable salts, and their prodrugs of formula:

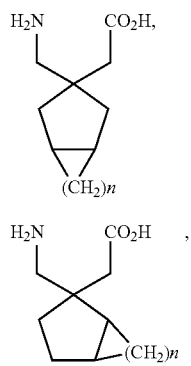

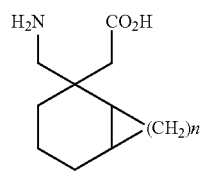

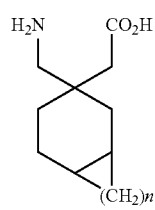

wherein n is an integer of from 1 to 4, where there are stereocentres, each center may be independently R or S, preferred compounds being those of Formulae I–IV above in which n is an integer of from 2 to 4. The compounds are disclosed as being useful in treating a variety of disorders including epilepsy, faintness attacks, hypokinesia, cranial disorders, neurodegenerative disorders, depression, anxiety, panic, pain, neuropathological disorders, and sleep disorders.

Patent application number EP 01400214.1 discloses the use of compounds of formula I to IV above for preventing and treatment of visceral pain, and gastrointestinal disorders.

More recently, International Patent Application Number PCT/IB02/01146 (unpublished at the priority date of the present invention, published as WO02/085839), incorporated herein by reference, describes cyclic amino acids of formulae (I)–(XXV):

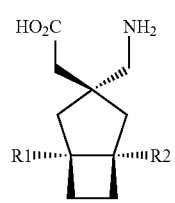

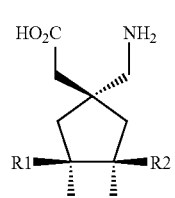

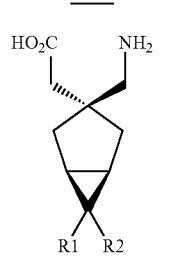

-continued
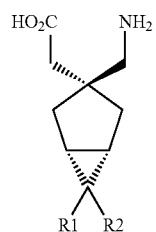
(IV)
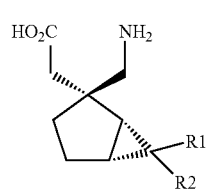
(V)
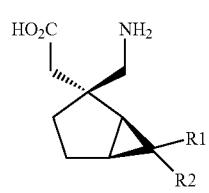
(VI)
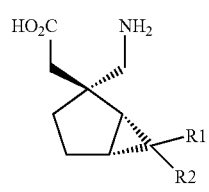
(VII)
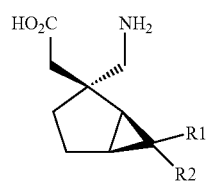
(VIII)
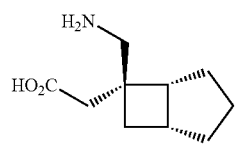
(IX)
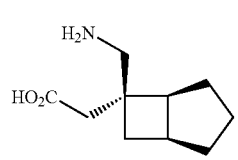
(X)
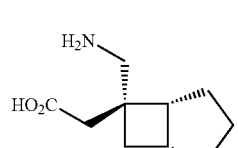
(XI)
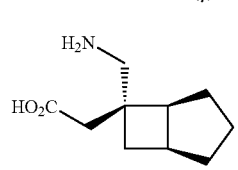
(XII)
-continued
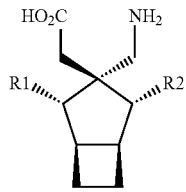
(XIII)
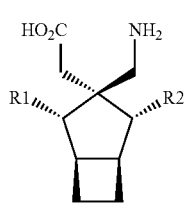
(XIV)
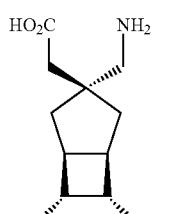
(XV)
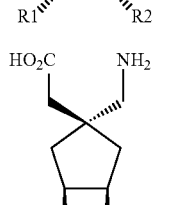
(XVI)
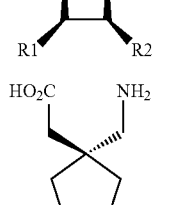
(XVII)
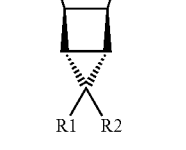
XVIII
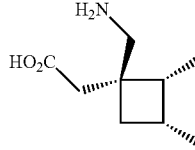
XIX
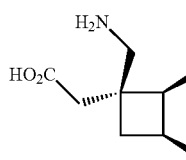
XX
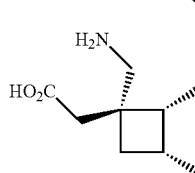

-continued

XXI

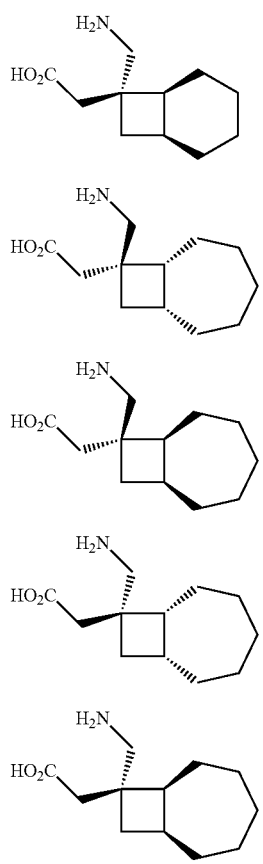

XXII

XXIII

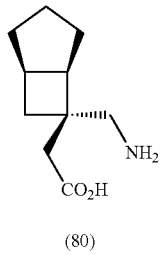

(80)

The application also discloses, as Method F, preparation of the following compounds:

XXIV

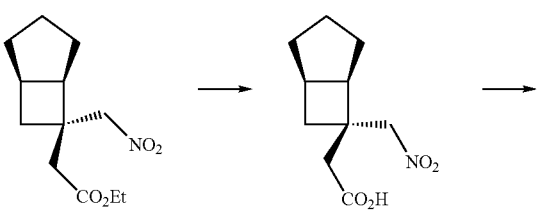

(70)    (71)

XXV

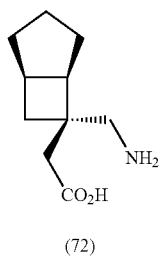

(72)

wherein $R^1$ and $R^2$ are each independently selected from H, straight or branched alkyl of 1–6 carbon atoms, cycloalkyl of from 3–6 carbon atoms, phenyl and benzyl, subject to the proviso that, except in the case of a tricyclooctane compound of formula (XVII), $R^1$ and $R^2$ are not simultaneously hydrogen; for use in the treatment of a number of indications, including pain. The application discloses, as Method H, preparation of the following compounds:

The compound of formula (70) may be prepared by Method A described in PCT/IB02/01146, illustrated here from compound (9), a known compound, see L. Y. Chen, L. Ghosez, *Tetrahedron Letters*, 1990, 31, 4467; C. Houge, A. M. Frisque-Hesbain, A. Mockel, L. Ghosez, J. P. Declercq, G. Germain, M. Van Meerssche, J. Am. Chem. Soc., 1982, 104, 2920.

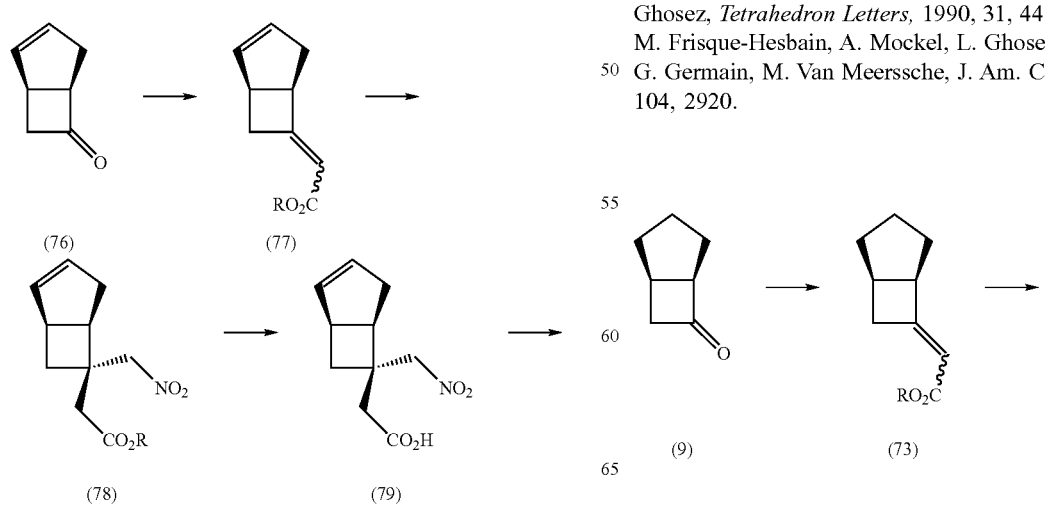

-continued

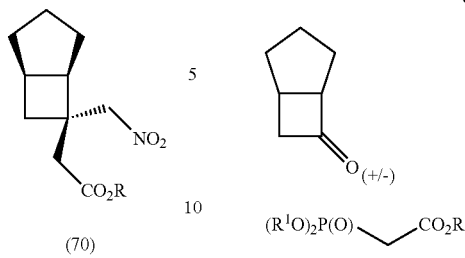

(70)

Compounds of formula (73) have been described in Hoffmann, H. M. R.; Ismail, Zeinhom M.; Weber, Anette. Dep. Chem., Univ. Hannover, Hannover, Fed. Rep. Ger. Tetrahedron Lett. (1981), 22(21), 1953–6.

The inventors now propose the racemic mixtures of a compound of formula (73) or (77) above and new processes for the manufacture of compounds (73) or (77), which may be used in the synthesis of therapeutic compounds disclosed in PCT/IB02/01146.

SUMMARY OF THE INVENTION

The present invention provides a racemic intermediate of formula (I) or (IA):

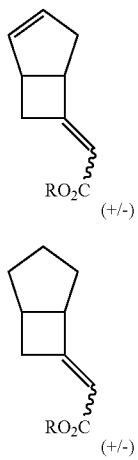

where R represents H or a suitable carboxylic acid protecting group, such as $C_{1-6}$ alkyl or benzyl.

As a further aspect, the invention provides a process for the preparation of a compound of formula (I) or (IA), comprising reaction of a compound of formula (II) or (IIA), respectively, with a compound of formula (III)

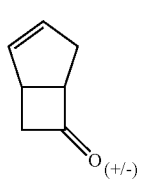

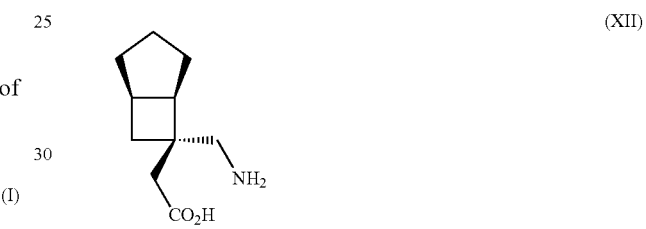

where $R^1$ represents a suitable phosphonyl ether group, such as $C_{1-6}$alkyl, and R represents a suitable carboxylic acid protecting group, such as $C_{1-6}$alkyl or benzyl, followed by optional deprotection of the R group.

The compounds of formula (I) & (IA) are useful in the preparation of therapeutic compounds disclosed in PCT/IB02/01146. As a preferred aspect, the present invention provides the use of a compound of formula (I) or (IA) in the preparation of a therapeutic compound of formula (XII)

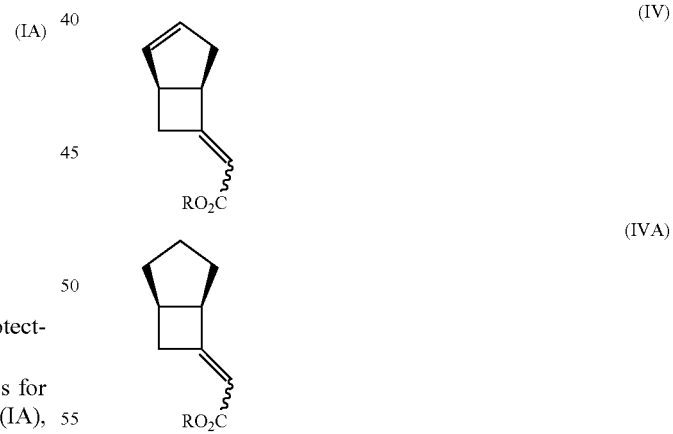

As a yet further aspect of the present invention, there is provided a process for the preparation of an intermediate compound of formula (IV) or (IVA)

where R represents H or a suitable carboxylic acid protecting group, such as $C_{1-6}$ alkyl or benzyl, comprising:
(i) where R is H, enzymatic hydrolysis of a compound of formula (I) or (IA) where R is a carboxylic acid protecting group; or
(ii) where R is a carboxylic acid protecting group, enzymatic esterification a compound of formula (I) or (IA) where R is H; or
(iii) chromatographic resolution of the isomers of a compound of formula (I) or (IA); or (iv) where R is a carboxylic acid protecting group, by enzymatic hydrolysis of a compound of formula (I) or (IA) where R is a carboxylic acid protecting group, followed by re-esterification; or (v) where R is a carboxylic acid protecting group, by removal of the undesired stereoisomer of a compound of formula (I) or (IA) where R is a carboxylic acid protecting group by enzymatic hydrolysis.

Sutiable carboxylic acid protecting groups are well known to those skilled in the art and include $C_{1-6}$ alkyl or benzyl groups or related derivatives. Suitable protecting groups are described in 'Protective Groups In Organic Synthesis', $3^{rd}$ Edn., by Greene and Wuts, Wiley Interscience Publishing, ISBN 0-471-16019-9, particularly the list of substituted methyl esters, 2-substituted ethyl esters, 2,6-dialkylphenyl esters, substituted benzyl esters, silyl esters, activated esters, miscellaneous derivatives, stannyl esters, amides and hydrazides at page 369–372 and the description, with references, from page 372–422, which is incorporated herein by reference.

Suitable enzymes for enzymatic hydrolysis include Altus 13, Altus 57, Chirazyme L2 solution, Thermomyces Langinosus or Mucor Meihei, preferably Novozyme 435.

A suitable compound of formula (1) is selected from:
(+/−) Ethyl bicyclo[3.2.0]hept-2-en-6-ylideneacetate; and
(+/−) Bicyclo[3.2.0]hept-2-en-6-ylideneacetic acid;
A suitable compound of formula (IA) is selected from:
(+/−) Ethyl bicyclo[3.2.0]hept-6-ylideneacetate; and
(+/−) Bicyclo[3.2.0]hept-6-ylideneacetic acid.

The present compounds can exist in unsolvated forms as well as solvated forms, including hydrated forms. In general, the solvated forms, including hydrated forms, which may contain isotopic substitutions (e.g. D2O, d6-acetone, d6-DMSO), are equivalent to unsolvated forms and are encompassed within the scope of the present invention.

The compounds of the present invention possess one or more chiral centers. Separation of diastereoisomers or cis and trans isomers may be achieved by conventional techniques, e.g. by fractional crystallisation, chromatography or H.P.L.C. of a stereoisomeric mixture of a compound of the invention or a suitable salt or derivative thereof. An individual enantiomer of a compound of the invention may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base, as appropriate.

The compounds of the invention may form base salts. Suitable base salts are formed from bases which form non-toxic salts and examples are the sodium, potassium, aluminium, calcium, magnesium, zinc, choline, diolamine, olamine, arginine, glycine, tromethamine, benzathine, lysine, meglumine and diethylamine salts. Salts with quaternary ammonium ions can also be prepared with, for example, the tetramethyl-ammonium ion.

Also included within the present scope of the compounds of the invention are polymorphs thereof.

The therapeutic compounds formed from the intermediates of the present invention are useful as agents for treating or relieving the symptoms of neurodegenerative disorders. Such neurodegenerative disorders include, for example, Alzheimer's disease, Huntington's disease, Parkinson's disease, and Amyotrophic Lateral Sclerosis. The present invention also covers treating neurodegenerative disorders termed acute brain injury. These include but are not limited to: stroke, head trauma, and asphyxia. Stroke refers to a cerebral vascular disease and may also be referred to as a cerebral vascular accident (CVA) and includes acute thromboembolic stroke. Stroke includes both focal and global ischemia. Also, included are transient cerebral ischemic attacks and other cerebral vascular problems accompanied by cerebral ischemia. These vascular disorders may occur in a patient undergoing carotid endarterectomy specifically or other cerebrovascular or vascular surgical procedures in general, or diagnostic vascular procedures including cerebral angiography and the like. Other incidents are head trauma, spinal cord trauma, or injury from general anoxia, hypoxia, hypoglycemia, hypotension as well as similar injuries seen during procedures from embole, hyperfusion, and hypoxia. The instant invention would be useful in a range of incidents, for example, during cardiac bypass surgery, in incidents of intracranial hemorrhage, in perinatal asphyxia, in cardiac arrest, and status epilepticus.

The therapeutic compounds described are also useful for the general treatment of pain, particularly neuropathic pain. Physiological pain is an important protective mechanism designed to warn of danger from potentially injurious stimuli from the external environment. The system operates through a specific set of primary sensory neurones and is exclusively activated by noxious stimuli via peripheral transducing mechanisms (Millan 1999 Prog. Neurobio. 57: 1–164 for an integrative Review). These sensory fibres are known as nociceptors and are characterised by small diameter axons with slow conduction velocities. Nociceptors encode the intensity, duration and quality of noxious stimulus and by virtue of their topographically organised projection to the spinal cord, the location of the stimulus. The nociceptors are found on nociceptive nerve fibres of which there are two main types, A-delta fibres (myelinated) and C fibres (non-myelinated). The activity generated by nociceptor input is transferred after complex processing in the dorsal horn, either directly or via brain stem relay nuclei to the ventrobasal thalamus and then on to the cortex, where the sensation of pain is generated.

Intense acute pain and chronic pain may involve the same pathways driven by pathophysiological processes and as such cease to provide a protective mechanism and instead contribute to debilitating symptoms associated with a wide range of disease states. Pain is a feature of many trauma and disease states. When a substantial injury, via disease or trauma, to body tissue occurs the characteristics of nociceptor activation are altered. There is sensitisation in the periphery, locally around the injury and centrally where the nociceptors terminate. This leads to hypersensitivity at the site of damage and in nearby normal tissue. In acute pain these mechanisms can be useful and allow for the repair processes to take place and the hypersensitivity returns to normal once the injury has healed. However, in many chronic pain states, the hypersensitivity far outlasts the healing process and is normally due to nervous system injury. This injury often leads to maladaptation of the afferent fibres (Woolf & Salter 2000 Science 288: 1765–1768). Clinical pain is present when discomfort and abnormal sensitivity feature among the patient's symptoms. Patients tend to be quite heterogeneous and may present with various pain symptoms. There are a number of typical pain subtypes: 1) spontaneous pain which may be dull, burning, or stabbing; 2) pain responses to noxious stimuli are exaggerated (hyperalgesia); 3) pain is produced by normally innocuous stimuli (allodynia) (Meyer et al., 1994 Textbook of Pain 13–44). Although patients with back pain, arthritis pain, CNS trauma, or neuropathic pain may have similar symptoms, the underlying mechanisms are different and, therefore, may require different treatment strategies. Therefore pain can be divided into a number of different areas because of differing pathophysiology, these include nociceptive, inflammatory, neuropathic pain etc. It should be noted that some types of pain have multiple aetiologies and thus can be classified in more than one area, e.g. Back pain, Cancer pain have both nociceptive and neuropathic components.

Nociceptive pain is induced by tissue injury or by intense stimuli with the potential to cause injury. Pain afferents are activated by transduction of stimuli by nociceptors at the site of injury and sensitise the spinal cord at the level of their termination. This is then relayed up the spinal tracts to the brain where pain is perceived (Meyer et al., 1994 Textbook of Pain 13–44). The activation of nociceptors activates two types of afferent nerve fibres. Myelinated A-delta fibres transmitted rapidly and are responsible for the sharp and stabbing pain sensations, whilst unmyelinated C fibres transmit at a slower rate and convey the dull or aching pain. Moderate to severe acute nociceptive pain is a prominent feature of, but is not limited to pain from strains/sprains, post-operative pain (pain following any type of surgical procedure), posttraumatic pain, burns, myocardial infarction, acute pancreatitis, and renal colic. Also cancer related acute pain syndromes commonly due to therapeutic interactions such as chemotherapy toxicity, immunotherapy, hormonal therapy and radiotherapy. Moderate to severe acute nociceptive pain is a prominent feature of, but is not limited to, cancer pain which may be tumour related pain, (e.g. bone pain, headache and facial pain, viscera pain) or associated with cancer therapy (e.g. postchemotherapy syndromes, chronic postsurgical pain syndromes, post radiation syndromes), back pain which may be due to herniated or ruptured intervertebral discs or abnormalities of the lumber facet joints, sacroiliac joints, paraspinal muscles or the posterior longitudinal ligament.

Neuropathic pain is defined as pain initiated or caused by a primary lesion or dysfunction in the nervous system (IASP definition). Nerve damage can be caused by trauma and disease and thus the term 'neuropathic pain' encompasses many disorders with diverse aetiologies. These include but are not limited to, Diabetic neuropathy, Post herpetic neuralgia, Back pain, Cancer neuropathy, HIV neuropathy, Phantom limb pain, Carpal Tunnel Syndrome, chronic alcoholism, hypothyroidism, trigeminal neuralgia, uremia, or vitamin deficiencies. Neuropathic pain is pathological as it has no protective role. It is often present well after the original cause has dissipated, commonly lasting for years, significantly decreasing a patients quality of life (Woolf and Mannion 1999 Lancet 353: 1959–1964). The symptoms of neuropathic pain are difficult to treat, as they are often heterogeneous even between patients with the same disease (Woolf & Decosterd 1999 Pain Supp. 6: S141–S147; Woolf and Mannion 1999 Lancet 353: 1959–1964). They include spontaneous pain, which can be continuous, or paroxysmal and abnormal evoked pain, such as hyperalgesia (increased sensitivity to a noxious stimulus) and allodynia (sensitivity to a normally innocuous stimulus).

The inflammatory process is a complex series of biochemical and cellular events activated in response to tissue injury or the presence of foreign substances, which result in swelling and pain (Levine and Taiwo 1994: Textbook of Pain 45–56). Arthritic pain makes up the majority of the inflammatory pain population. Rheumatoid disease is one of the commonest chronic inflammatory conditions in developed countries and rheumatoid arthritis is a common cause of disability. The exact aetiology of RA is unknown, but current hypotheses suggest that both genetic and microbiological factors may be important (Grennan & Jayson 1994 Textbook of Pain 397–407). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder 2002 Ann Pharmacother. 36: 679–686; McCarthy et al., 1994 Textbook of Pain 387–395). Most patients with OA seek medical attention because of pain. Arthritis has a significant impact on psychosocial and physical function and is known to be the leading cause of disability in later life. Other types of inflammatory pain include but are not limited to inflammatory bowel diseases (IBD).

Other types of pain include but are not limited to:

Musculo-skeletal disorders including but not limited to myalgia, fibromyalgia, spondylitis, sero-negative (non-rheumatoid) arthropathies, non-articular rheumatism, dystrophinopathy, Glycogenolysis, polymyositis, pyomyositis;

Central pain or 'thalamic pain' as defined by pain caused by lesion or dysfunction of the nervous system including but not limited to central post-stroke pain, multiple sclerosis, spinal cord injury, Parkinson's disease and epilepsy;

Heart and vascular pain including but not limited to angina, myocardial infarction, mitral stenosis, pericarditis, Raynaud's phenomenon, scleredoma, scleredoma, skeletal muscle ischemia;

Visceral pain, and gastrointestinal disorders. The viscera encompasses the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders include the functional bowel disorders (FBD) and the inflammatory bowel diseases (IBD). These GI disorders include a wide range of disease states that are currently only moderately controlled, including—for FBD, gastro-esophageal reflux, dyspepsia, the irritable bowel syndrome (IBS) and functional abdominal pain syndrome (FAPS), and—for IBD, Crohn's disease, ileitis, and ulcerative colitis, which all regularly produce visceral pain. Other types of visceral pain include the pain associated with dysmenorrhea, pelvic pain, cystitis and pancreatitis;

Head pain including but not limited to migraine, migraine with aura, migraine without aura cluster headache, tension-type headache;

Orofacial pain including but not limited to dental pain, temporomandibular myofascial pain.

The therapeutic compounds are also expected to be useful in the treatment of anxiety and of panic as demonstrated by means of standard pharmacological procedures.

The biological activity of the therapeutic compounds of the invention may be measured in a radioligand binding assay using [$^3$H]gabapentin and the $\alpha_2\delta$ subunit derived from porcine brain tissue (Gee N. S., Brown J. P., Dissanayake V. U. K., Offord J., Thurlow R., Woodruff G. N., *J. Biol. Chem.*, 1996; 271:5879–5776). Results may be expressed in terms of μM or nM $\alpha 2\delta$ binding affinity.

The therapeutic compounds can be administered, for example but not limited to the following route: orally, buccally or sublingually in the form of tablets, capsules, multi- and nano-particulates, gels, films (incl. muco-adhesive), powder, ovules, elixirs, lozenges (inc. liquid-filled), chews, solutions, suspensions and sprays. The compounds of the invention may also be administered as osmotic dosage form, or in the form of a high energy dispersion or as coated particles or fast-dissolving, fast-disintegrating dosage form as described in Ashley Publications, 2001 by Liang and Chen The therapeutic compounds can also be administered by injection, that is, intravenously, intramuscularly, intracutaneously, intraduodenally, or intraperitoneally, intraarterially, intrathecally, intraventricularly, intraurethrally, intrasternally, intracranially, intraspinally or subcutaneously, or they may be administered by infusion, needle-free injectors or implant injection techniques.

Also, the therapeutic compounds can be administered intranasally or by inhalation.

Alternatively, the therapeutic compounds may be administered topically to the skin, mucosa, dermally or transdermally, for example, in the form of a gel, hydrogel, lotion, solution, cream, ointment, dusting powder, dressing, foam, film, skin patch, wafers, implant, sponges, fibres, bandage, microemulsions and combinations thereof.

Alternatively, the therapeutic compounds can be administered rectally, for example in the form of a suppository or pessary. They may also be administered by vaginal route.

The therapeutic compounds may also be administered by the ocular route. They may also be administered in the ear, using for example but not limited to the drops.

The therapeutic compounds may also be used in combination with a cyclodextrin. Alpha-, beta- and gamma-cyclodextrins are most commonly used and suitable examples are described in WO-A-91/11172, WO-A-94/02518 and WO-A-98/55148.

The term 'administered' includes delivery by viral or non-viral techniques. Viral delivery mechanisms include but are not limited to adenoviral vectors, adeno-associated viral (AAV) vectors, herpes viral vectors, retroviral vectors, lentiviral vectors, and baculoviral vectors. Non-viral delivery mechanisms include lipid mediated transfection, lipsomes, immunoliposomes, lipofectin, cationic facial amphiphiles (CFAs) and combinations thereof. The routes for such delivery mechanisms include but are not limited to mucosal, nasal, oral, parenteral, gastrointestinal, topical or sublingual routes.

The pharmaceutical preparation of the therapeutic compounds is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsules, tablet, cachet, or lozenge itself, or it can be the appropriate number of any of these in packaged form. The quantity of active component in a unit dose preparation may be varied or adjusted from 0.1 mg to 1 g according to the particular application and the potency of the active component. In medical use the drug may be administered three times daily as, for example, capsules of 100 or 300 mg. In therapeutic use, the compounds utilized in the pharmaceutical method of this invention are administered at the initial dosage of about 0.01 mg to about 100 mg/kg daily. A daily dose range of about 0.01 mg to about 100 mg/kg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The invention is illustrated by the following non-limiting examples.

EXAMPLE 1

(+/−)-Ethyl bicyclo[3.2.0]hept-2-en-6-ylideneacetate

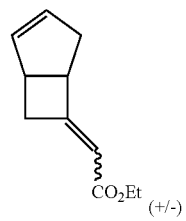

A solution of triethylphosphonoacetate (10.7 g; 48 mmol) in tetrahydrofuran (5 ml) was added to a suspension of 60% sodium hydride dispersion (1.91 g; 48 mmol) in tetrahydrofuran (30 ml) maintaining the temperature between 5–15° C. A solution of bicyclo[3.2.0]hept-2-en-6-one (5 g; 46 mmol) in tetrahydrofuran (5 ml) was added maintaining the temperature between 5–15° C. The reaction mixture was stirred at ambient temperature for 30 minutes then demineralised water (30 ml) added. The phases are separated and toluene (20 ml) was added to the organic layer which was washed with demineralised water (2×20 ml). The organic phase was dried over anhydrous magnesium sulfate, filtered and concentrated in vacuo to yield the title compound as a oil (7.74 g).

$^1$H-NMR (400 MHz, CDCl$_3$): δ=5.84–5.61 (3H, m), 4.16–4.11 (2H, q), 3.91–3.61 (1H, m), 3.45–3.39 (1H, m), 3.32–3.06 (1H, m), 2.92–2.76 (1H, m), 2.69–2.62 (1H, m), 2.53–2.42 (1H, m), 1.29–1.25 (3H, t).

EXAMPLE 2

(1S,5R)-Bicyclo[3.2.0]hept-2-en-6-ylideneacetic acid

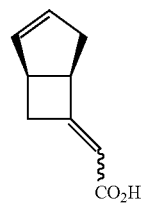

The racemic ester (1.0 g; 5.6 mmol) of example 1 was dissolved in tert-butanol (4 ml) and potassium phosphate buffer (pH=7.2; 6 ml). The resulting slurry was stirred for 5 minutes at 30° C. Novozyme 435 (500 mg), immobilized *Candida Antarctica* lipase B, was added to the reaction and the suspension was then stirred at the 30° C. for 10 hours. The heterogeneous mixture was filtered to recover the immobilized enzyme. The filtrate was extracted three times with ethyl acetate (100 ml) to remove the undesired enantiomer as the ester. The aqueous solution was then acidified to pH 3.5 with dilute hydrochloric acid and extracted three times with ethyl acetate (100 ml), the combined organic phases were dried with sodium sulfate and concentrated in vacuo to give the title compound.

EXAMPLE 3

(1S,5R)-Ethyl bicyclo[3.2.0]hept-2-en-6-ylideneacetate

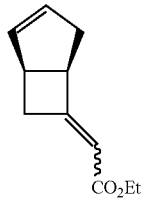

The compound of Example 2 was dissolved in ethanol (20 ml) and concentrated sulfuric acid was added. The reaction was heated to 80° C. and stirred for 18 hours. The solvent was removed in vacuo to yield the title compound as an oil.

$^1$H-NMR (400 MHz, CDCl$_3$): δ=5.84–5.61 (3H, m), 4.16–4.11 (2H, q), 3.91–3.61 (1H, m), 3.45–3.39 (1H, m), 3.32–3.06 (1H, m), 2.92–2.76 (1H, m), 2.69–2.62 (1H, m), 2.53–2.42 (1H, m), 1.29–1.25 (3H, t).

EXAMPLE 4

(+/−)-Ethyl bicyclo[3.2.0]hept-6-ylideneacetate

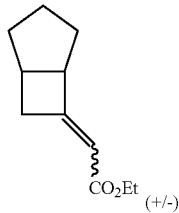

Triethylphosphonoacetate (96.2 g; 429 mmol) was added to a suspension of 60% sodium hydride dispersion (16.5 g; 413 mmol) in tetrahydrofuran (480 mL) maintaining the temperature between 1–4° C. A solution of bicyclo[3.2.0] heptan-6-one (35.0 g; 318 mmol) in tetrahydrofuran (320 ml) was added maintaining the temperature between 5–15° C. The reaction mixture was stirred at ambient temperature overnight. Demineralised water (350 mL) added and the product was extracted with diethyl ether (3×450 ml). The combined organic phases were washed with brine (300 ml), dried over anhydrous magnesium sulfate, filtered and concentrated in vacuo to leave a pale orange oil. This was purified by chromatography on a silica pad, eluting with 1:19 ethyl acetate:n-hexane. The product containing fractions were combined and concentrated in vacuo to yield the title compound as a colourless oil (47.8 g).

$^1$H-NMR (400 MHz, CDCl$_3$): δ=5.55 (1H, d), 4.15 (2H, q), 3.40 (1H, m), 3.20 (1H, m), 2.90 (1H, m), 2.55 (1H, m), 1.8–1.5 (6H, m), 1.30 (3H, t).

EXAMPLE 5

(1R,5R)-Bicyclo[3.2.0]hept-6-ylideneacetic acid

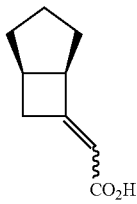

The racemic ester of Example 4 (200 g; 1.11 mol) was added to a stirred solution of acetone (0.80 L) and potassium phosphate buffer (pH=7.2; 1.2 L). The hazy solution was stirred at 20–25° C. and Novozyme 435 (50 g), immobilized *Candida Antarctica* lipase B, was added to the reaction mixture. The suspension was then stirred at 20–25° C. for 120 hours. During this time a 1M aqueous solution of sodium hydroxide was added so as to maintain a pH of 8.1. Concentrated hydrochloric acid (45 ml) was added to pH 2–3 and the heterogeneous reaction mixture was filtered. The filter cake was washed with n-heptane (1.0 L). The two phase filtrate was separated and the aqueous phase re-extracted with tert-butylmethyl ether (0.50 L). The combined organic phases were extracted with a 1M aqueous solution of sodium hydroxide (0.4 L). The aqueous solution was then adjusted to pH 1–2 by the addtion of concentrated hydrochloric acid (40 ml) and extracted twice with tert-butylmethyl ether (0.40 L, then 0.20 L). The combined organic phases were washed with demineralised water (0.40 L) and concentrated in vacuo to give the title compound (56.5 g) in 33.5% yield as a pale yellow oil which crystallised on standing.

$^1$H-NMR (400 MHz, CDCl$_3$): δ=5.79–5.54 (1H, m), 3.75–3.40 (1H, m), 3.25–3.18 (1H, m), 2.94–2.83 (1H, m), 2.61–2.26 (1H, m), 1.84–1.52 (6H, m).

EXAMPLE 6

(1R,5R)-Ethyl bicyclo[3.2.0]hept-6-ylideneacetate

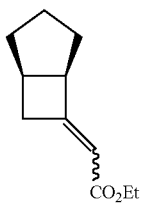

The compound of Example 5 (10.5 Kg; 69.0 mol) was dissolved in absolute ethanol (52.5 L) and 98 wt % sulfuric acid (0.525 Kg; 5.36 mol) was added at 20–25° C. The reaction mixture was then heated to 75° C. over 0.5 hours and stirred for 24 hours. The reaction mixture was cooled to 10° C. and a 40 wt % solution of sodium hydroxide (3.17 L) diluted with demineralised water (28.6 L) was added slowly to maintain the reaction temperature below 20° C. n-Hep tane (31.5 L) was added and the phases were separated. The aqueous phase was then extracted again with n-heptane (31.5 L). The combined organic phases were washed twice with demineralised water (63.0 L, then 31.5 L). The organic phase was separated to give the title compound (11.1 Kg) in 89% yield as an organic solution which is used directly in the next step.

$^1$H-NMR (400 MHz, CDCl$_3$): δ=5.55 (1H, d), 4.15 (2H, q), 3.40 (1H, m), 3.20 (1H, m), 2.90 (1H, m), 2.55 (1H, m), 1.8–1.5 (6H, m), 1.30 (3H, t).

EXAMPLE 7

Ethyl (1R,5R,6S)-[6-(nitromethyl)bicyclo[3.2.0]hept-6-yl]acetate

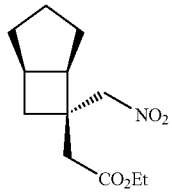

The n-heptane solution (12.5 L) of the acrylic ester of Example 6 (0.921 Kg; 5.11 mol) was concentrated by distillation at atmospheric pressure to 36% of its original volume. The n-heptane was then replaced with tetrahydrofuran by atmospheric azeotropic distillation at constant volume. The reaction mixture was cooled to 20–25° C., then tetrabutylammonium fluoride trihydrate (2.10 Kg; 6.64 mol) and nitromethane (0.499 Kg, 8.18 mol) were added. The resulting brown solution was stirred at 20–25° C. for 17 hours. To the reaction mixture a 2M aqueous solution of hydrochloric acid (4.5 L) was added, causing the reaction temperature to rise by 8° C. n-Heptane (4.5 L) was added and the phases were separated. The organic layer was then washed with demineralised water (4.5 L) to give the title product (1.08 Kg) in 88% yield as an organic solution which is used directly in the next step.

$^1$H-NMR (400 MHz, CDCl$_3$): δ=4.80 (2H, m), 4.15 (2H, m), 2.85 (1H, m), 2.65 (1H, m), 2.55 (2H, m), 2.20 (1H, m), 1.9–1.4 (7H,m), 1.25 (3H, t).

EXAMPLE 8

(1R,5R,6S)-[6-(Nitromethyl)bicyclo[3.2.0]hept-6-yl] acetic acid

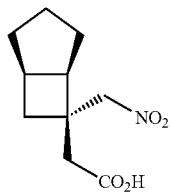

The n-heptane from the organic solution of the nitro ester of Example 7 (1.08 Kg; 4.49 mol) was replaced with tetrahydrofuran by azeotropic distillation at atmospheric pressure and constant volume. The solution was cooled to +25° C. and a solution of sodium hydroxide (0.359 Kg; 8.98 mol) in demineralised water (4.5 L) was added and the reaction stirred for 16 hours. n-Heptane (4.5 L) was added and the phases were separated. The aqueous phase was adjusted to pH 2–4 by the addition of concentrated hydrochloric acid (0.8 L) giving a suspension. The aqueous phase was extracted with ethyl acetate (9.6 L) to give the title product (0.928 Kg) in 97% yield as an organic solution which is used directly in the next step.

$^1$H-NMR (400 MHz, CDCl$_3$): δ=4.80 (2H, m), 2.85 (1H, m), 2.60 (3H, m), 2.20 (1H, m), 1.85 (1H, m), 1.70 (2H, m), 1.6–1.4 (4H, m).

EXAMPLE 9

(1R,5R,6S)-[6-(Aminomethyl)bicyclo[3.2.0]hept-6-yl]acetic acid

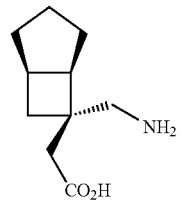

The cyclohexylamine salt of the nitro acid of Example 10 (100 g; 320 mmol) was added to a mixture of ethyl acetate (680 ml) and a 2M aqueous solution of hydrochloric acid (340 ml). The mixture was stirred vigorously for 10 minutes and the phases were separated. The organic layer was further washed with demineralised water (340 ml). The organic layer was separated and demineralised water (1360 ml) was added, to this two phase mixture 5% platinum on carbon as a 50% water wet catalyst (13.65 g) was added. The reaction mixture was then hydrogenated at 50° C. and a hydrogen pressure of 150 psi for 24 hours. The hydrogen was purged with nitrogen and the reaction mixture was heated to 70° C. The reaction mixture was filtered through Celite at 70° C. and the filter pad was washed with hot demineralised water (50 ml). The filtrate was allowed to settle and phases were separated at 70° C., the lower aqueous phase was removed and concentrated by distillation at atmospheric pressure to a sixth of its original volume. The white slurry was cooled to 50° C. and isopropanol (705 ml) was then added over a period of 1.7 hours. The white slurry was then cooled to between +5° C. and +10° C. over 90 minutes and stirred for 2.5 hours. The solid was collected by filtration and the damp filter cake washed with isopropanol (60 ml). The isolated solid was then dried in vacuo at 45° C. for 18 hours to give the title compound in high purity as a white crystalline solid (36.3 g) in 62% yield.

$^1$H-NMR (400 MHz, d$_6$-DMSO): δ=7.94 (3H, br s), 3.15 (1H, d), 3.07 (1H, d), 2.72 (1H, quin), 2.46 (1H, m), 2.42 (1H, d), 2.33 (1H, d), 1.98 (1H, m), 1.80–1.64 (2H, m), 1.59 (1H, m), 1.48–1.28 (3H, m), 1.23 (1H, dd).

EXAMPLE 10

(1R,5R,6S)-[6-(Nitromethyl)bicyclo[3.2.0]hept-6-yl] acetic acid cyclohexylamine salt

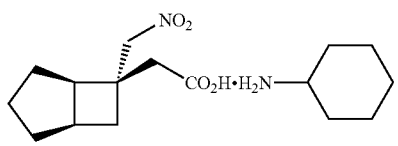

A solution of nitro acid of Example 8 (928 g; 4.35 mol) in ethyl acetate (9.6 L) was dried by atmospheric azeotropic distillation at constant volume. After cooling the solution to 40° C., cyclohexylamine (423 g; 4.26 mol) was added over 15 minutes. The resultant slurry was cooled to 20° C. over 4 hours and left to stir for 13 hours at 20° C. The solid was collected by filtration and the damp filter cake washed with ethyl acetate (1.3 L). The isolated solid was then dried in vacuo at 30° C. for 18 hours to give the title compound as a white solid (1.205 Kg) in 91% yield.

Melting point: 140.4–141.6° C. (decomposed) $^1$H-NMR (400 MHz, $d_6$-DMSO): δ=4.95 (2H, dd), 2.72 (2H, m), 2.20–2.00 (3H, m), 1.90–1.70 (7H, m), 1.55 (1H, m), 1.45–1.00 (10H, m).

The invention claimed is:

1. A process for the preparation of a compound of formula (IV) or (IVA)

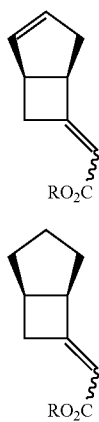

from a compound of formula (I) or (IA)

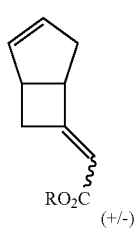

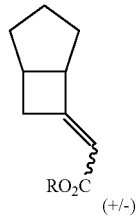

where R represents H or a suitable carboxylic acid protecting group comprising the reaction:
   (i) where R is H, enzymatic hydrolysis of a compound of formula (I) or (IA), where R is a carboxylic acid protecting group; or
   (ii) where R is a carboxylic acid protecting group, enzymatic esterification of a compound of formula (I) or (IA) where R is H; or
   (iii) chromatographic resolution of the isomers of a compound of formula (I) or (IA); or
   (iv) where R is a carboxylic acid protecting group, by enzymatic hydrolysis of a compound of formula (I) or (IA) where R is a carboxylic acid protecting group, followed by re-esterificarion; or
   (v) where R is a carboxylic acid protecting group, by removal of the undesired stereoisomer of a compound of formula (I) or (IA) where R is a carboxylic acid protecting group by enzymatic hydrolysis.

2. The process according to claim 1 or (iv) where the enzymatic hydrolysis is effected by Novozyrne 435.

3. The process of converting a compound of formula (I)

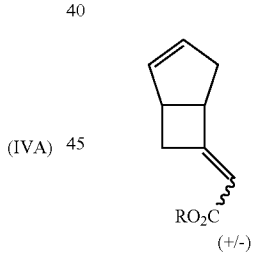

wherein R represents H or a carboxylic acid protecting group, to a compound of formula (XII)

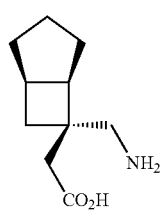

which comprises, as an intermediate step, the process according to claim 1, followed by the steps:

(a) nicromethane is added to a compound of formula (IV)

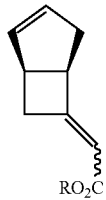
(IV)

by a Michael addition reaction with a suitable base to give a compound of formula (78);

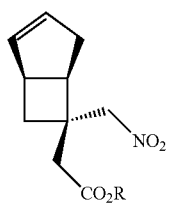
(78)

(b) the compound of formula (78) is hydrolyzed with a suitable base to give a compound of formula (79)

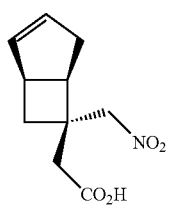
(79)

(c) the compound of formula (79) is reduced by hydrogenation.

4. The process of converting a compound of formula (IA)

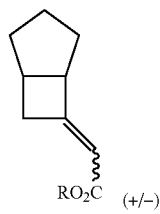
(IA)

wherein R represents H or a carboxylic acid protecting group, to a compound of formula (XII)

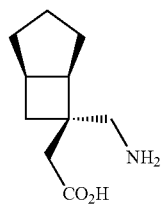
(XII)

which comprises, as an intermediate step, the process according to claim 1, followed by the steps:

(a) nitromethane is added to a compound of formula (IVA)

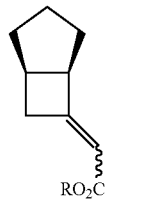
(IVA)

by a Michael addition reaction with a suitable base to give a compound of formula (74)

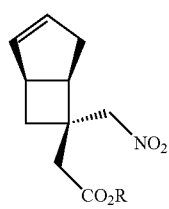
(74)

(b) the compound of formula (74) is reduced by catalytic hydrogenation in a suitable solvent.

* * * * *